United States Patent
Kim et al.

(10) Patent No.: US 12,116,284 B2
(45) Date of Patent: Oct. 15, 2024

(54) ENERGY-EFFICIENT SYSTEM AND METHOD FOR CARBON DIOXIDE CONVERSION

(71) Applicant: KOREA RESEARCH INSTITUTE OF CHEMICAL TECHNOLOGY, Daejeon (KR)

(72) Inventors: Seok Ki Kim, Daejeon (KR); Ki Won Jun, Daejeon (KR); Hae Gu Park, Daejeon (KR); Sun Mi Hwang, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 909 days.

(21) Appl. No.: 17/053,577

(22) PCT Filed: May 29, 2019

(86) PCT No.: PCT/KR2019/006437
§ 371 (c)(1),
(2) Date: Nov. 6, 2020

(87) PCT Pub. No.: WO2019/231237
PCT Pub. Date: Dec. 5, 2019

(65) Prior Publication Data
US 2021/0230005 A1    Jul. 29, 2021

(30) Foreign Application Priority Data

May 30, 2018    (KR) ........................ 10-2018-0061859

(51) Int. Cl.
*C01B 32/40* (2017.01)
*C07C 1/04* (2006.01)
*B01J 23/78* (2006.01)
*C07C 9/04* (2006.01)

(52) U.S. Cl.
CPC ............ *C01B 32/40* (2017.08); *C07C 1/0485* (2013.01); *B01J 23/78* (2013.01); *B01J 2231/641* (2013.01); *C07C 9/04* (2013.01)

(58) Field of Classification Search
CPC ..................................................... C01B 32/40
See application file for complete search history.

(56) References Cited

U.S. PATENT DOCUMENTS

2007/0149392 A1    6/2007    Ku et al.

FOREIGN PATENT DOCUMENTS

| CN | 107530683 A | 1/2018 |
|---|---|---|
| KR | 10-2011-0013968 A | 2/2011 |
| KR | 10-2011-0127489 A | 11/2011 |
| KR | 10-1626800 B1 | 6/2016 |
| KR | 10-1706639 B1 | 2/2017 |
| KR | 10-2018-0004165 A | 1/2018 |
| KR | 10-2018-0043864 A | 5/2018 |
| WO | 2007-130081 A1 | 11/2007 |
| WO | 2017/130081 A1 | 8/2017 |

OTHER PUBLICATIONS

International Search Report dated Sep. 10, 2019, in connection with corresponding International Patent Application No. PCT/KR2019/006437.
PCT Written Opinion dated Oct. 9, 2019, in connection with corresponding International Patent Application No. PCT/KR2019/006437.
Chinese Office Action issued on Nov. 16, 2022, in connection with the Chinese Patent Application No. 201980028950.6, 13 pages.

*Primary Examiner* — Stuart L Hendrickson
(74) *Attorney, Agent, or Firm* — Hauptman Ham, LLP (57) ABSTRACT

A system and method for converting carbon dioxide are proposed. The system for converting carbon dioxide includes a carbon monoxide generator for generating carbon monoxide through a reverse water gas shift reaction and a hydrocarbon generator for producing a hydrocarbon through a Fischer-Tropsch synthesis reaction, whereby the carbon monoxide generator is packed both with a catalyst for the reverse water gas shift reaction and with a catalyst for the Fischer-Tropsch synthesis reaction, thus increasing the CO yield in the carbon monoxide generator even at a low temperature compared to when the catalyst for the reverse water gas shift reaction is used alone, ultimately increasing the hydrocarbon yield in the hydrocarbon generator. Moreover, the energy of the exothermic Fischer-Tropsch synthesis reaction can be used as the energy required for the endothermic reverse water gas shift reaction, thereby increasing energy efficiency and processing yield and thus reducing operation and maintenance costs.

10 Claims, 7 Drawing Sheets

ENERGY-EFFICIENT SYSTEM AND METHOD FOR CARBON DIOXIDE CONVERSION

CROSS REFERENCE TO RELATED APPLICATION

This present application is a national stage filing under 35 U.S.C § 371 of PCT application number PCT/KR2019/006437 filed on May 29, 2019 which is based upon and claims the benefit of priority to Korean Patent Application No. 10-2018-0061859 filed on May 30, 2018 in the Korean Intellectual Property Office. The disclosures of the above-listed applications are hereby incorporated by reference herein in their entirety.

BACKGROUND OF THE DISCLOSURE

1. Technical Field

The present disclosure relates to a system and method for converting carbon dioxide into a more useful compound, and more particularly to a system and method for converting carbon dioxide, in which the energy necessary for the reaction for conversion of carbon dioxide into a hydrocarbon through hydrogenation of carbon dioxide may be efficiently reduced and a product may be obtained at a high yield.

2. Description of the Related Art

Coal and petroleum are fossil energy, which accounts for more than 50% of all energy that is used, and have been important energy sources for humankind in past centuries, and carbon dioxide, which is thermodynamically stable and results from various processes for converting coal and petroleum into energy, has been discharged without a separate post-treatment process.

However, carbon dioxide has recently come to be known as the main greenhouse gas, which accounts for 55% of global warming, and thus various techniques for removing carbon dioxide have been proposed. Among these, techniques for converting carbon dioxide into value-added chemical materials or gaseous or liquid fuels using catalysts are specifically being considered.

Among these chemical techniques for conversion of carbon dioxide, the method of producing a hydrocarbon such as an alpha olefin or the like by hydrogenating carbon dioxide using a catalyst is the most preferred because it enables technical linkage with existing industrial processes, has a large market for products, and is capable of easily processing a large amount of carbon dioxide.

The reaction mechanism for the synthesis of hydrocarbons through the reaction for conversion of carbon dioxide using hydrogen has not yet been completely elucidated, but is generally known to proceed through a two-step continuous reaction. Specifically, the reaction for conversion of carbon dioxide includes a first step, in which carbon dioxide supplied as a reactant is converted into carbon monoxide through a reverse water gas shift (RWGS) reaction, and a second step, in which the carbon monoxide thus obtained is coupled with hydrogen through a Fischer-Tropsch synthesis (FTS) reaction and is thus converted into a hydrocarbon (olefin, etc.). The first- and second-step reactions are carried out in separate reactors, and water generated in the first step is removed.

The reverse water gas shift reaction in the first step is endothermic, and may be represented as Scheme 1 below.

$$CO_2 + H_2 > CO + H_2O \quad \Delta RH_{300}^O = 38 KJ/mol \quad (1)$$

The reverse water gas shift reaction in the first step is reversible, and the reverse reaction thereof (reaction from CO and $H_2O$ to $CO_2$ and $H_2$) is known as a water gas shift reaction. The reverse water gas shift reaction may be carried out under conditions that enable partial conversion of $CO_2$ and $H_2$, resulting in a total product mixture including carbon monoxide (CO) and $H_2O$. Then, the carbon monoxide obtained in the first step is subjected to a Fischer-Tropsch synthesis (FTS) reaction in the second step. The FTS reaction is exothermic, and may be represented as Scheme 2 below.

$$CO + 2H_2 \rightarrow CH_2 + H_2O \quad \Delta RH_{300}^O = -166 KJ/mol \quad (2)$$

In Scheme 2, "$CH_2$" represents a general hydrocarbon moiety that may be incorporated into a larger molecule, such as ethylene ($C_2H_4$) or propylene ($C_3H_6$).

Meanwhile, since the reverse water gas shift reaction is endothermic, the higher the temperature, the more favorable the reaction, and many reactions actually proceed at high temperatures. Since the equilibrium conversion of the reverse water gas shift reaction is only 13.8% ($CO_2:H_2=1:1$) under typical reaction conditions of 300° C. and 1 MPa, in order to increase the reaction rate or the equilibrium conversion, the reaction temperature is typically set to 600° C. or higher so that sufficient energy is supplied (Korean Patent No. 10-1706639 and Korean Patent Application Publication No. 10-2018-0004165).

Various techniques for providing an energy source for the reverse water gas shift reaction process have been developed and applied in practice, and a heating furnace is the most commonly used. The heating furnace enables heating to a high temperature of 600° C. or more and is thus suitable as a preheating device for the reverse water gas shift reaction, but is disadvantageous because controlling the temperature is difficult and also because a process using a combustible gas is accompanied by high risk. Moreover, selective heating depending on the location or portion of the reactor is impossible, a temperature gradient between the outside and the inside of the reactor is formed, and portions that are locally heated are formed, resulting in thermal cracking as a side reaction. This side reaction decreases the carbon monoxide yield and is a main cause of reduced processing performance, so controlling heating conditions becomes a very important variable. Also, since the subsequent FTS reaction (step 2) operates at a relatively low temperature ranging from 200° C. to 300° C., a temperature difference of 300° C. to 400° C. occurs between the reactions in the first and second steps. Even when a heat exchanger having high efficiency is provided therebetween, thermal efficiency is inevitably decreased.

Accordingly, International Publication No. WO 2017-130081 discloses a method of converting carbon dioxide including providing a reactor having a first reaction zone in which carbon monoxide is synthesized from carbon dioxide and a second reaction zone in which a hydrocarbon material is synthesized from carbon monoxide, in which the temperature conditions are controlled in the first and second reaction zones, with the goal of preparing an olefin from carbon dioxide in order to increase the supplied energy reaction efficiency and carbon efficiency.

However, the aforementioned document is problematic in that a steep temperature gradient is formed between the outside and the inside of the reactor because heating to a high temperature needs to be performed in order to generate carbon monoxide, and also in that cracking occurs due to the formation of the portion that is locally heated, undesirably lowering the carbon yield.

SUMMARY OF THE DISCLOSURE

Accordingly, the present disclosure has been made keeping in mind the problems encountered in the related art, and an objective of the present disclosure is to provide a system and method for converting carbon dioxide capable of improving the overall energy efficiency of the process and the processing yield and thus reducing operation and maintenance costs.

In order to accomplish the above objective, an aspect of the present disclosure provides a system for converting carbon dioxide, including a carbon monoxide generator including: a case having an inlet, into which carbon dioxide and hydrogen are introduced, formed in one side and an outlet, from which a reaction product is discharged, formed in an opposite side; and a catalytic reactor disposed in the internal space of the case and packed with both a catalyst for a reverse water gas shift reaction and a catalyst for a Fischer-Tropsch synthesis reaction so that the reverse water gas shift reaction and the Fischer-Tropsch synthesis reaction are carried out together, thereby increasing a carbon monoxide yield and allowing the reaction heat generated in the Fischer-Tropsch synthesis reaction to be used for the reverse water gas shift reaction.

In an embodiment of the present disclosure, the system for converting carbon dioxide may further include a remover disposed downstream of the carbon monoxide generator and receiving a reaction product from the carbon monoxide generator to separate and remove at least one of $H_2O$ and a hydrocarbon from the reaction product; and a hydrocarbon generator disposed downstream of the remover, packed with a catalyst for a Fischer-Tropsch synthesis reaction, and receiving a gaseous material from the remover to thus carry out the Fischer-Tropsch synthesis reaction.

Also, in an embodiment of the present disclosure, the catalyst for the Fischer-Tropsch synthesis reaction that is charged in the carbon monoxide generator may be a catalyst including Fe and further including at least one selected from among Cu, K, Co, Zn and Al.

Also, in an embodiment of the present disclosure, the catalytic reactor of the carbon monoxide generator may be configured such that a catalyst layer packed with the catalyst for the reverse water gas shift reaction and a catalyst layer packed with the catalyst for the Fischer-Tropsch synthesis reaction are repeatedly and alternately stacked one or more times or such that the catalyst for the reverse water gas shift reaction and the catalyst for the Fischer-Tropsch synthesis reaction are uniformly mixed. Alternatively, the catalytic reactor of the carbon monoxide generator may be configured such that the internal space thereof is divided into at least two reaction zones by a partition wall or a reaction tube, and each of the reaction zones is packed with the catalyst for the reverse water gas shift reaction or the catalyst for the Fischer-Tropsch synthesis reaction, in which the reaction zones adjacent to each other are packed with different catalysts, or such that the internal space thereof is divided into at least two reaction zones by a partition wall or a reaction tube, and a catalyst layer packed with the catalyst for the reverse water gas shift reaction and a catalyst layer packed with the catalyst for the Fischer-Tropsch synthesis reaction are repeatedly and alternately stacked one or more times in each of the reaction zones, in which the catalyst layers located at the same height in reaction zones adjacent to each other are packed with different catalysts.

In the catalytic reactor of the carbon monoxide generator, the catalyst for the Fischer-Tropsch synthesis reaction and the catalyst for the reverse water gas shift reaction may be present at a mass ratio ranging from 1:99 to 99:1, and the catalyst for the reverse water gas shift reaction may include at least one metal selected from the group consisting of Cu, Li, Rh, Mo, Pt, Ce and Pd.

Another aspect of the present disclosure provides a method of converting carbon dioxide using hydrogen, including: generating carbon monoxide by introducing carbon dioxide and hydrogen into a reactor packed with both a catalyst for a reverse water gas shift reaction and a catalyst for a Fischer-Tropsch synthesis reaction.

The method of converting carbon dioxide may further include, after the generating the carbon monoxide: separating and removing at least one of $H_2O$ and a hydrocarbon from a reaction product obtained in the generating the carbon monoxide; and producing a hydrocarbon using a catalyst for a Fischer-Tropsch synthesis reaction from a gaseous material obtained after the removing the at least one of $H_2O$ and the hydrocarbon.

In an embodiment of the present disclosure, the generating the carbon monoxide may be performed at a reaction temperature of 300 to 475° C., and the producing the hydrocarbon may be performed at a reaction temperature of 200 to 350° C.

Also, in a preferred embodiment of the present disclosure, the generating the carbon monoxide may be performed using a reactor configured such that the catalyst for the reverse water gas shift reaction and the catalyst for the Fischer-Tropsch synthesis reaction are uniformly mixed, or using a reactor configured such that a catalyst layer for the reverse water gas shift reaction and a catalyst layer for the Fischer-Tropsch synthesis reaction are repeatedly and alternately stacked one or more times, in which the catalyst layers are arranged such that carbon dioxide and hydrogen introduced into the reactor first come into contact with the catalyst layer for the reverse water gas shift reaction.

According to the present disclosure, in a system for converting carbon dioxide including a carbon monoxide generator for generating CO from $CO_2$ through a reverse water gas shift reaction, when the carbon monoxide generator is packed not only with a catalyst for a reverse water gas shift reaction but also with a catalyst for a Fischer-Tropsch synthesis reaction, the CO yield in the carbon monoxide generator can be increased compared to when the catalyst for the reverse water gas shift reaction is used alone, ultimately increasing the hydrocarbon yield in a hydrocarbon generator, thereby improving overall processing productivity.

In addition, according to the present disclosure, the reaction heat of the exothermic Fischer-Tropsch synthesis reaction can be directly used for the endothermic reverse water gas shift reaction, whereby the supply of energy to the reverse water gas shift reaction can be reduced, thus maximizing energy efficiency.

In addition, according to the present disclosure, the reaction heat of the Fischer-Tropsch synthesis reaction can be directly used for the endothermic reverse water gas shift reaction, whereby the carbon monoxide generator can operate in an adiabatic state without the need to supply energy, making it possible to minimize or eliminate a heat supply device for the reverse water gas shift reaction, a cooler for removing the reaction heat generated in a Fischer-Tropsch synthesis reactor, a heat exchanger, and the like. Therefore, the entire reaction system can be simplified, and the carbon monoxide yield in the carbon monoxide generator can be increased, so there is an effect of maximizing the yield in the subsequent Fischer-Tropsch synthesis reaction.

DESCRIPTION OF SPECIFIC EMBODIMENTS

Unless otherwise defined, all technical and scientific terms used herein have the same meanings as those typically understood by those skilled in the art to which the present disclosure belongs. Generally, the nomenclature used herein is well known in the art and is typical.

As used herein, when any part is said to "comprise" or "include" any element, this does not mean that other elements are excluded, and such other elements may be further included unless otherwise specifically mentioned.

As used herein, the term "reaction zone" refers to an internal space of a catalytic reactor in which reactive gases containing carbon dioxide gas, hydrogen gas and the like come into contact with a catalyst on a catalyst layer.

As used herein, the terms "first", "second", etc. are only used to distinguish one element from another when the names of the elements are the same, and the order thereof is not necessarily limited in the following description.

The present disclosure pertains to a system for converting carbon dioxide including a carbon monoxide generator for generating carbon monoxide after introducing carbon dioxide gas and hydrogen gas thereto, in which the carbon monoxide generator is packed with a catalyst for a reverse water gas shift reaction (hereinafter referred to as a "RWGS catalyst") and with a catalyst for a Fischer-Tropsch synthesis reaction (hereinafter referred to as an "FTS catalyst"), whereby the carbon monoxide yield may be increased even at a relatively low temperature, and thus the hydrocarbon yield in the subsequent Fischer-Tropsch synthesis reaction may be increased, and simultaneously, the heat generated by the Fischer-Tropsch synthesis reaction may be used for the reverse water gas shift reaction in the carbon monoxide generator, thereby increasing energy efficiency.

The system for converting carbon dioxide according to the present disclosure may further include a remover, which is disposed downstream of the carbon monoxide generator promoting the reverse water gas shift reaction because the catalytic reactor is packed with the RWGS catalyst and the FTS catalyst, and which receives a reaction product from the carbon monoxide generator to separate and remove at least one of byproducts including $H_2O$ and hydrocarbons from the reaction product, and a hydrocarbon generator, which is disposed downstream of the remover, receives carbon monoxide and hydrogen from the remover, and is packed with an FTS catalyst to produce hydrocarbon through a Fischer-Tropsch synthesis reaction.

Thereby, the system for converting carbon dioxide according to the present disclosure is capable of increasing the carbon monoxide yield even at a relatively low temperature compared to when carbon monoxide is conventionally generated using the RWGS catalyst alone, and of simultaneously achieving two goals, namely efficient energy use and increased carbon yield, by suppressing the generation of byproducts in the carbon monoxide generator.

Hereinafter, the system for converting carbon dioxide according to the present disclosure is described in detail with reference to the accompanying drawings.

Figure 1:
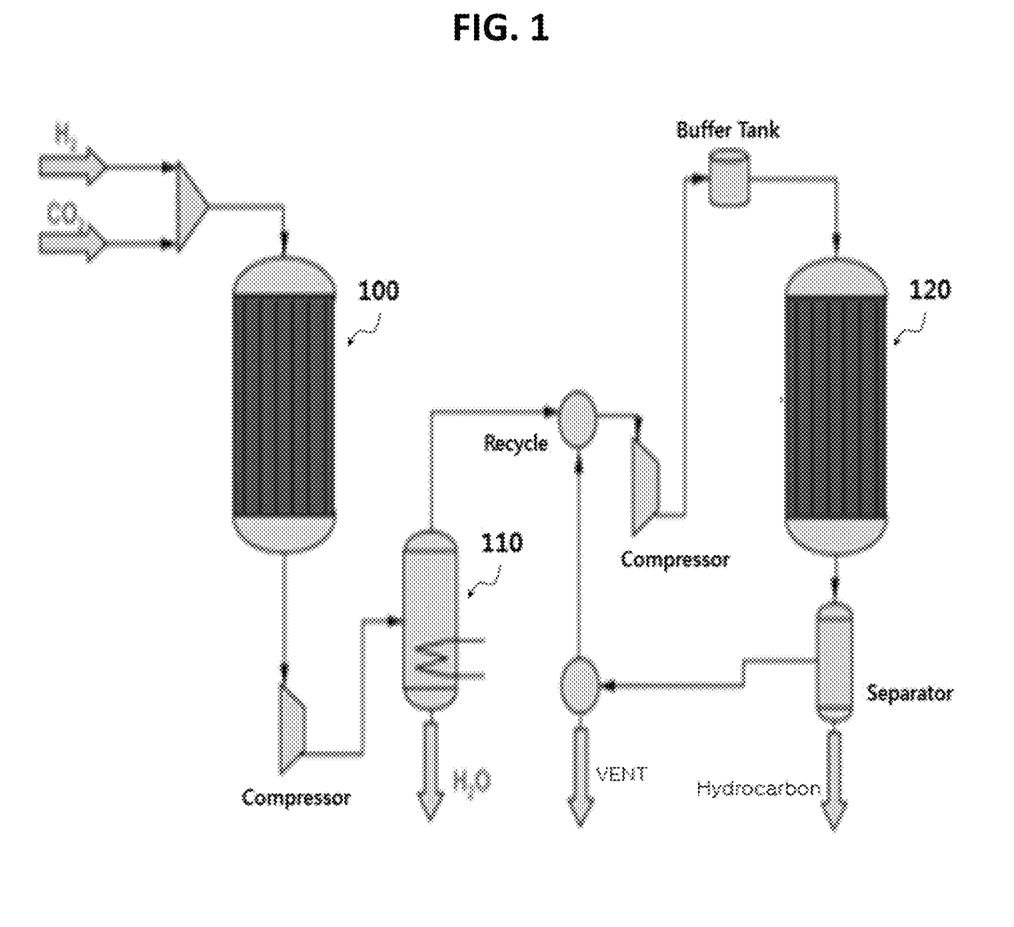
FIG. 1 schematically shows a system for converting carbon dioxide according to the present disclosure.
Figure 2:
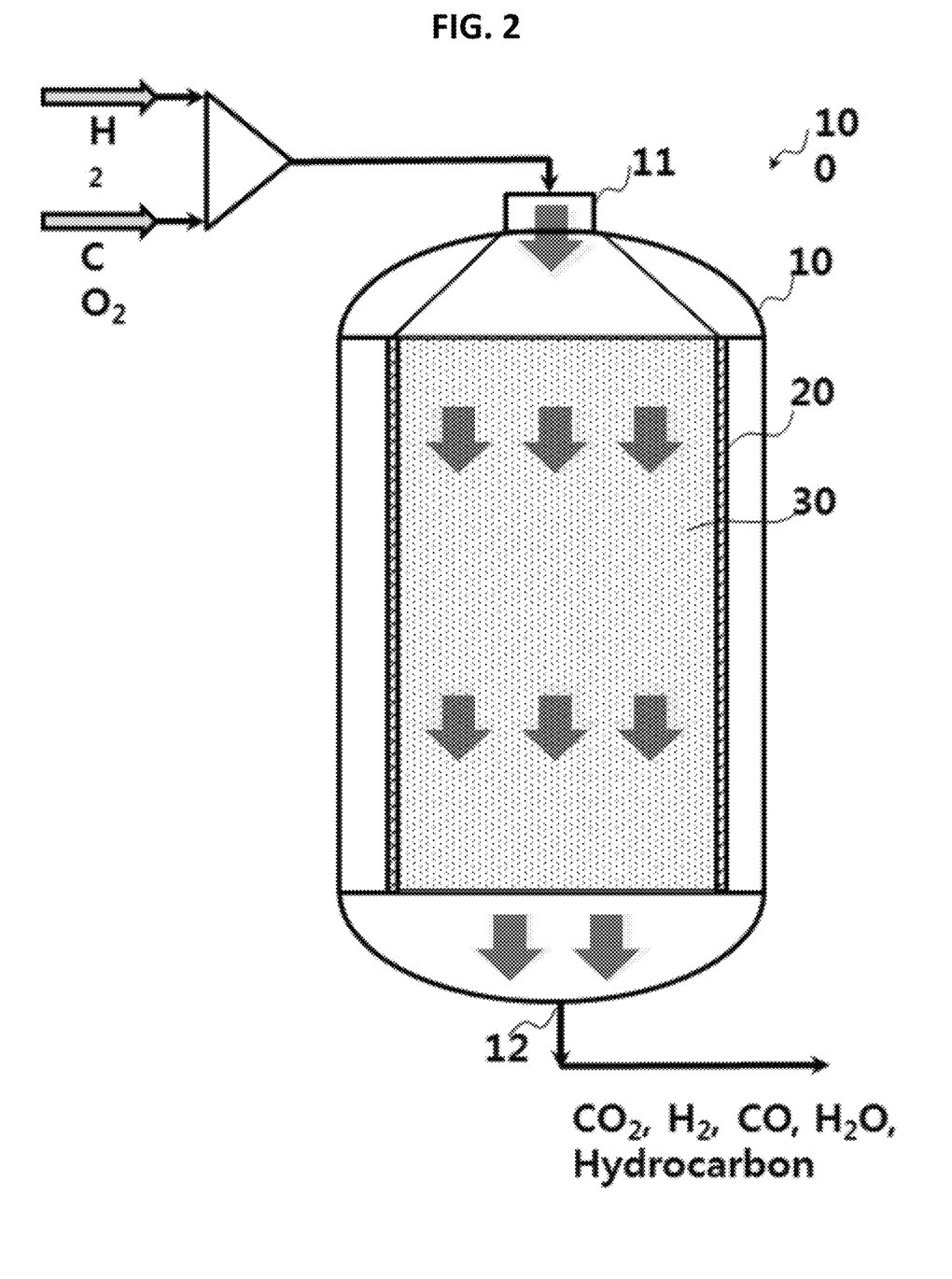
FIG. 2 is a schematic longitudinal cross-sectional view of a carbon monoxide generator according to an embodiment of the present disclosure.
Figure 3:
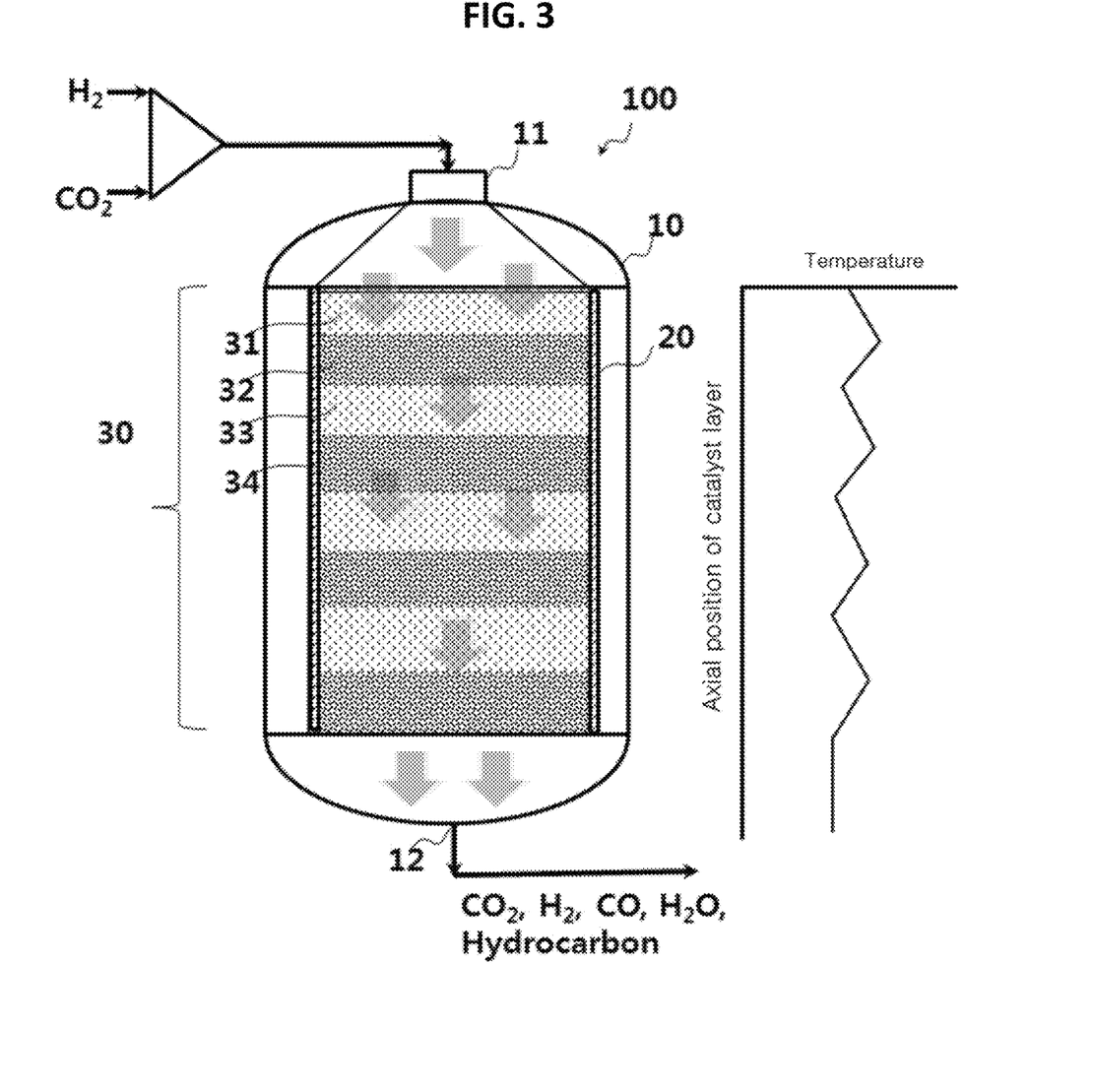
FIG. 3 is a schematic longitudinal cross-sectional view of a carbon monoxide generator according to another embodiment of the present disclosure.
Figure 4:
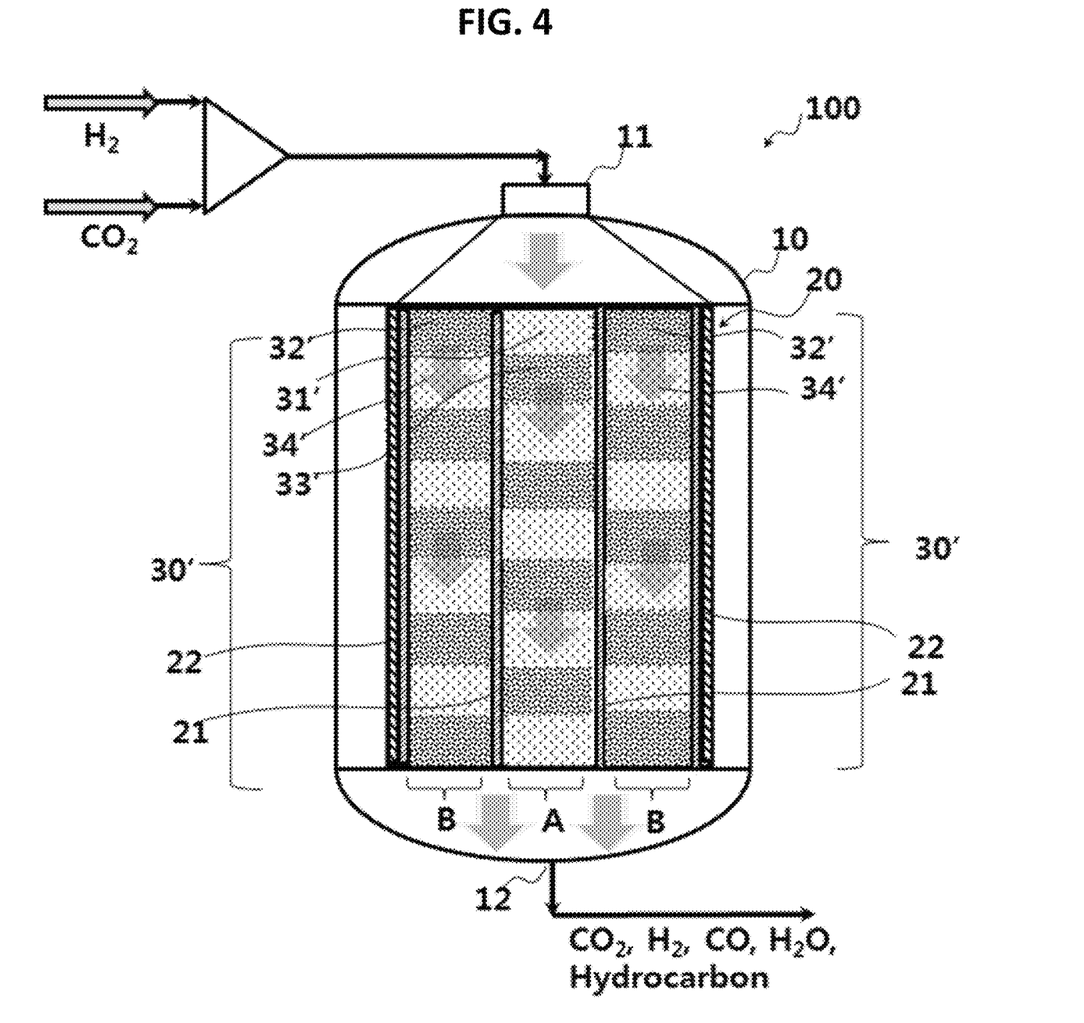
FIG. 4 is a schematic longitudinal cross-sectional view of a carbon monoxide generator according to still another embodiment of the present disclosure.
Figure 5:
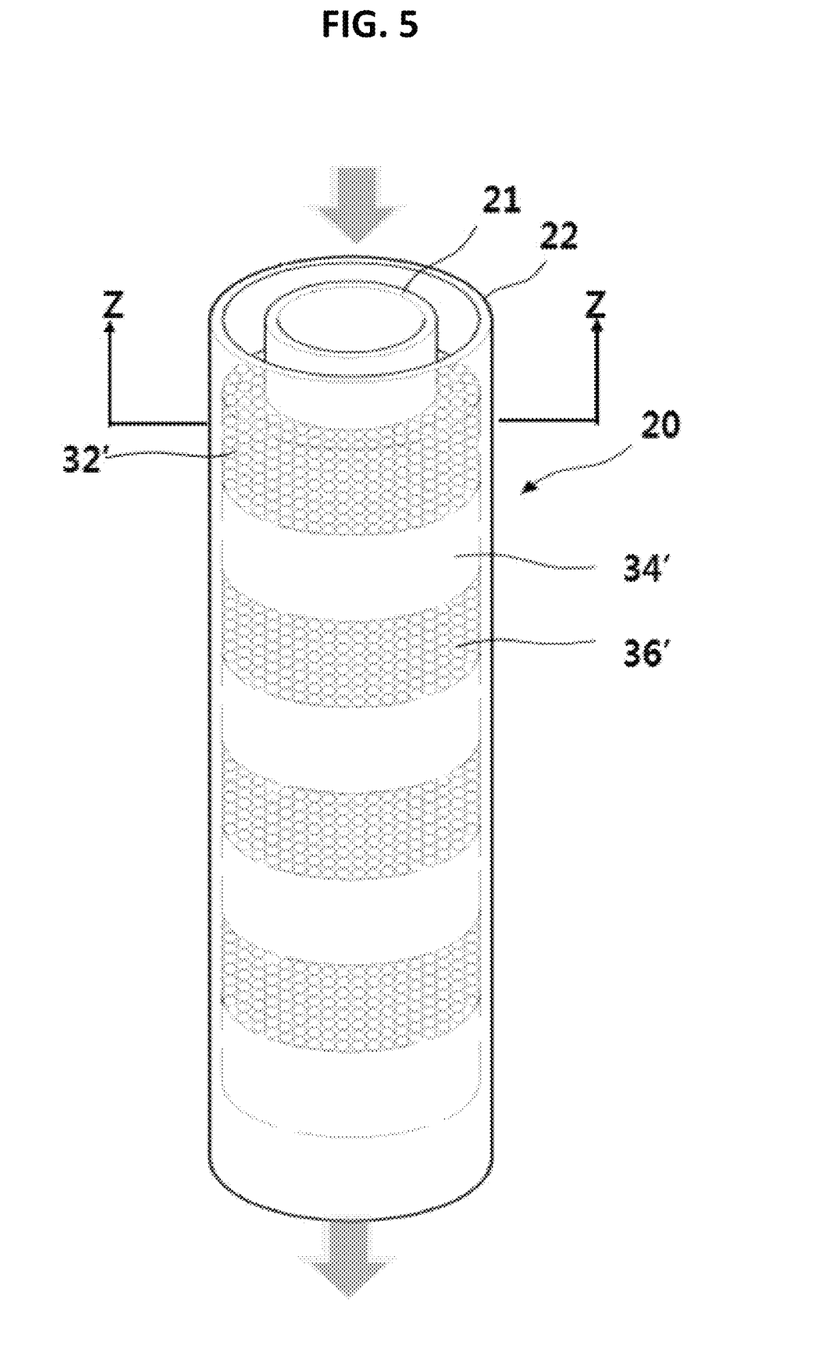
FIG. 5 is a perspective view of the catalyst reactor shown in FIG. 4.
Figure 6:
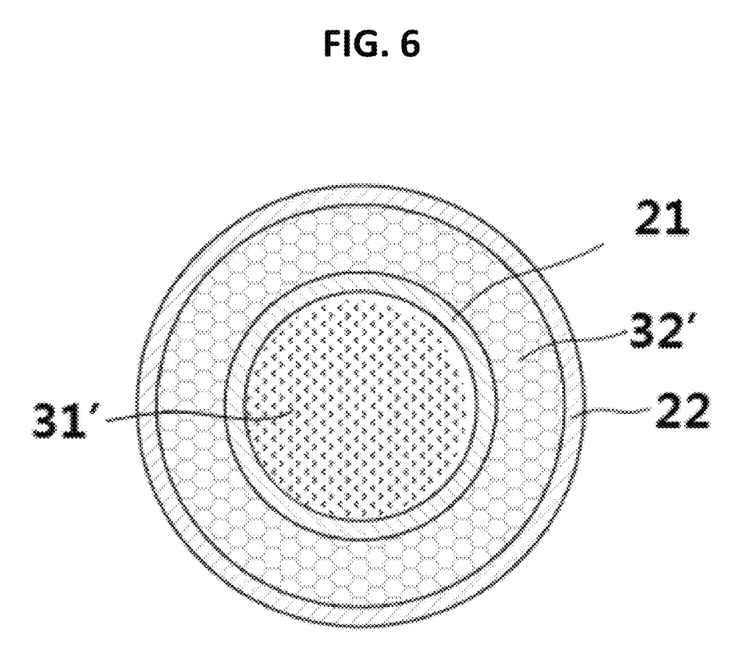
FIG. 6 is a cross-sectional view taken along the line Z-Z of FIG. 5.
Figure 7:
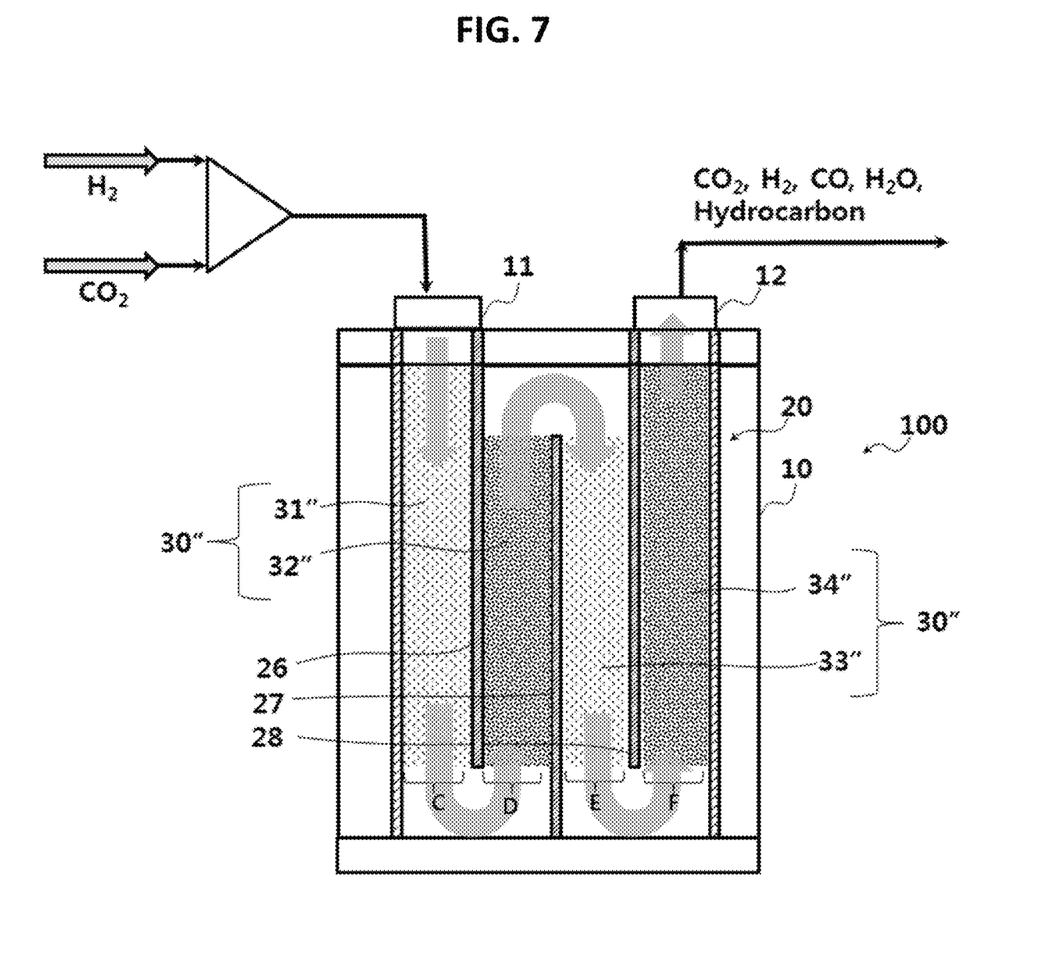
FIG. 7 is a schematic longitudinal cross-sectional view of a carbon monoxide generator according to yet another embodiment of the present disclosure.

FIG. 1 schematically shows the system for converting carbon dioxide according to an embodiment of the present disclosure, FIG. 2 is a schematic longitudinal cross-sectional view of a carbon monoxide generator according to an embodiment of the present disclosure, FIG. 3 is a schematic longitudinal cross-sectional view of a carbon monoxide generator according to another embodiment of the present disclosure, FIG. 4 is a schematic longitudinal cross-sectional view of a carbon monoxide generator according to still another embodiment of the present disclosure, FIG. 5 is a perspective view of the catalyst reactor shown in FIG. 4, FIG. 6 is a cross-sectional view taken along the line Z-Z of FIG. 5, and FIG. 7 is a schematic longitudinal cross-sectional view of a carbon monoxide generator according to yet another embodiment of the present disclosure.

The system for converting carbon dioxide according to the present disclosure includes a carbon monoxide generator 100 packed with both a RWGS catalyst and an FTS catalyst, and further includes a remover 110 disposed downstream of the carbon monoxide generator 100 and a hydrocarbon generator 120 disposed downstream of the remover 110.

In general, a system for converting carbon dioxide is configured to perform only a reverse water gas shift reaction in a carbon monoxide generator and only a Fischer-Tropsch synthesis reaction in a hydrocarbon generator, and is also configured such that the carbon monoxide generator operates at a temperature of about 600° C. and the hydrocarbon generator operates at a lower temperature.

However, in such a typical configuration, since the reaction heat for a reverse water gas shift reaction has to be continuously supplied to the carbon monoxide generator in which the reverse water gas shift reaction occurs, it is essential to provide an external heat supply device for electric heating, burner heating or the like.

Furthermore, the carbon monoxide generator, the temperature of which is relatively high, increases the difficulty of heat supply device and temperature control, so overall device costs are increased and ease of operation is reduced, and since the temperature difference between the carbon monoxide generator and the hydrocarbon generator reaches 300° C.-400° C., the use of a heat exchanger is essential, inevitably decreasing thermal efficiency, which is undesirable.

The inventors of the present disclosure have conducted studies to solve such problems, and have ascertained that, when the carbon monoxide generator is packed with both the RWGS catalyst and the FTS catalyst, it is possible to lower the temperature of the carbon monoxide generator, increase the carbon monoxide yield and suppress the generation of byproducts, and simultaneously, the use of energy in the carbon monoxide generator may be reduced because the energy required for the endothermic reverse water gas shift reaction is self-supplied using the heat generated during the Fischer-Tropsch synthesis reaction, thus culminating in the present disclosure.

In the system for converting carbon dioxide according to an embodiment of the present disclosure, the carbon monoxide generator 100 includes a case 10 and a catalytic reactor 20 so that a reverse water gas shift reaction and a Fischer-Tropsch synthesis reaction of carbon dioxide are carried out at the same time. The case 10 of the carbon monoxide generator is provided with an inlet 11, into which carbon dioxide gas and hydrogen gas are introduced, at one side, and an outlet 12, from which a reaction product is discharged, at an opposite side.

The case 10 may vary in dimension or shape depending on the production capacity, supply amount, and catalyst, and may be adjusted through various methods known to those skilled in the art, and is preferably exemplified by a vertical cylinder having an inlet 11 formed in one side, such as the upper portion thereof, so that reactants such as carbon dioxide gas and hydrogen gas are introduced thereto, and an outlet 12 formed in a side opposite the inlet, such as the lower portion thereof, whereby reaction products, such as hydrocarbons, water and the like, and unreacted carbon dioxide and hydrogen are discharged to the outside or downstream through the catalytic reactor 20, which will be described later.

The catalytic reactor 20 is disposed inside the case 10, and is packed with the RWGS catalyst and the FTS catalyst to obtain a hydrocarbon such as olefin, water, carbon monoxide and the like from carbon dioxide gas and hydrogen gas introduced from the inlet through the reaction for conversion of carbon dioxide.

Here, the catalytic reactor 20 may vary in dimension or shape depending on the production capacity, supply amount, and catalyst, and may be adjusted through various methods known to those skilled in the art, but is configured to include reaction zones (FIGS. 4 to 7) defined by partition walls 26, 27, 28 or reaction tubes 21, 22 in order to realize uniform reaction heat supply as well as high reaction heat transfer of the RWGS catalyst and the FTS catalyst that are charged in the catalytic reactor.

The partition walls 26, 27, 28 or the reaction tubes 21, 22 may be used without limitation, so long as they are typically used in a catalytic reaction process. In view of thermal conductivity, a metal such as stainless steel, iron-chromium alloy, molybdenum-nickel-chromium, or the like may be used therefor.

As for the RWGS catalyst and the FTS catalyst that are charged in the catalytic reactor, in order to efficiently transfer the reaction heat generated in the Fischer-Tropsch synthesis reaction to the RWGS catalyst, the catalyst layer may be provided in a form in which the RWGS catalyst and the FTS catalyst are physically mixed such that the RWGS catalyst and the FTS catalyst are uniformly distributed and the contact area therebetween is maximized, or alternatively, the RWGS catalyst layer and the FTS catalyst layer may be repeatedly and alternately stacked.

In addition, in order to promote heat transfer, a heat-conductive mesh (not shown), in which a metal for efficient heat transfer extends in a radial shape or the like, may be included. Through the heat-conductive radial mesh, heat may be more efficiently transferred from the FTS catalyst layer to the RWGS catalyst layer. The mesh may be formed in a radial shape, a mesh shape, a fin shape, etc. so as to enable efficient heat transfer, but is not limited thereto.

In an embodiment thereof, the RWGS catalyst and the FTS catalyst may be charged in a uniformly mixed state to form a monolayered catalyst layer 30 (FIG. 2). The monolayered catalyst layer 30 is configured such that the RWGS catalyst and the FTS catalyst are uniformly mixed, thereby maximizing the contact area between the RWGS catalyst and the FTS catalyst to thus efficiently transfer the reaction heat generated in the Fischer-Tropsch synthesis reaction to the RWGS catalyst.

For the above operation, depending on the relative activity of the RWGS catalyst and the FTS catalyst, the RWGS catalyst and the FTS catalyst are provided at a mass ratio of 1:99 to 99:1, preferably 10:90 to 90:10, and more preferably 30:70 to 70:30.

The mixing of the catalysts may be performed by uniformly mixing the RWGS catalyst and the FTS catalyst or alternately forming the RWGS catalyst layer and the FTS catalyst layer.

As the RWGS catalyst, a catalyst that predominantly promotes the RWGS reaction may be used. The RWGS catalyst may include, but is not limited to, at least one metal selected from the group consisting of Cu, Li, Rh, Mo, Pt, Ce, Pd, and the like. The catalyst may be used in the form of being supported on a support, and the appropriate support may be, but is not limited to, at least one selected from the group consisting of $Al_2O_3$, $SiO_2$, $CeO_2$, $La_2O_3$, $MO_2C$, $SiO_2$—$Al_2O_3$, carbon, and the like.

As the FTS catalyst, a catalyst that predominantly promotes the Fischer-Tropsch synthesis reaction may be used. The FTS catalyst may include at least one metal selected from Co, Fe, Ni, and Ru, and in some cases, the above metal may be added with at least one cocatalyst selected from the group consisting of K, Pt, Pd, Cu, Co, Zn, Al, etc. These catalysts may be used in the form of being supported on an appropriate support. The support may be, but is not limited to, at least one selected from the group consisting of $Al_2O_3$, $SiO_2$, $CeO_2$, $La_2O_3$, $Mo_2C$, $SiO_2$—$Al_2O_3$, carbon, and the like.

As the FTS catalyst, a catalyst that exhibits Fischer-Tropsch synthesis reaction activity and also has reverse water gas shift reaction activity is preferably used. The catalyst is configured such that the Fe-based material ($Fe_2O_3$, $Fe_3O_4$, Fe, $Fe_3C$, $Fe_5C_2$, etc.) is added with a cocatalyst including, but not being limited to, Cu, K, Co, Zn, Al, etc. For example, a catalyst such as FeCuKAl may be used, and Zn and Co may be substituted for Cu. The catalysts may be used in the form of being supported on an appropriate support, but the support is not limited, and may be at least one selected from the group consisting of $Al_2O_3$, $SiO_2$, and carbon.

The RWGS catalyst and the FTS catalyst may be repeatedly and alternately stacked to form a multilayered catalyst layer 30. For example, as shown in FIG. 3, the multilayered catalyst layer 30 may include a first catalyst layer 31 packed with the RWGS catalyst, a second catalyst layer 32 located under the first catalyst layer and packed with the FTS catalyst, a third catalyst layer 33 located under the second catalyst layer 32 and packed with the RWGS catalyst, and a fourth catalyst layer 34 located under the third catalyst layer 33 and packed with the FTS catalyst, which are formed in a manner in which the RWGS catalyst and the FTS catalyst are repeatedly and alternately stacked n times. Preferably, a total of two catalyst layers are formed by stacking one RWGS catalyst layer and one FTS catalyst layer.

In the catalyst layer configuration, pluralities of RWGS catalyst layers and FTS catalyst layers are formed adjacent to each other, whereby the reaction heat generated in the Fischer-Tropsch synthesis reaction may be efficiently supplied to the RWGS catalyst layer, thereby increasing energy efficiency.

As an example, when the RWGS catalyst layer and the FTS catalyst layer are alternately arranged, the reactive gas alternately comes into contact with the FTS catalyst layer and the RWGS catalyst layer while an endothermic reaction and an exothermic reaction are repeated, so the temperature state in each catalyst layer naturally changes, and the temperature change has the advantage of maintaining a temperature state favorable for the catalyst layer that is disposed downstream (the temperature state change on the right of FIG. 3).

As another example, the RWGS catalyst and the FTS catalyst may be charged in a catalytic reactor having two or more reaction zones defined by the partition walls 26, 27, 28 or the reaction tubes 21, 22, thus forming individual packing layers 30', 30". Here, the reaction tubes preferably divide the reaction zone into a multi-cylindrical structure that radially surrounds the longitudinal central axis of the catalytic reactor 20, and the partition walls may be arranged in the catalytic reactor without restriction, so long as they do not obstruct the flow path of reactive gases such as carbon dioxide, hydrogen and the like.

Specifically, the catalytic reactor 20 is configured such that a plurality of reaction zones A, B is defined by cylindrical reaction tubes composed of an inner reaction tube, an outer reaction tube, etc., and the RWGS catalyst and the FTS catalyst are repeatedly and alternately stacked n times in the plurality of reaction zones to form a plurality of catalyst layers 30'. Here, the catalyst layers stacked in one reaction zone defined as described above and in another, neighboring, reaction zone may be formed of different catalysts so as to realize efficient heat transfer and heat exchange by maximizing the contact area between the RWGS catalyst and the FTS catalyst.

As an example therefor, as shown in FIGS. 4 to 6, when the catalytic reactor 20 is configured such that the reaction zone A of the catalytic reactor defined by the inner reaction tube 21 is packed with the RWGS catalyst to form a first catalyst layer 31', a third catalyst layer 33' may be formed by packing FTS catalyst under the first catalyst layer formed as described above, after which the RWGS catalyst and the FTS catalyst may be sequentially and alternately stacked in the reaction zone A in the same manner. Meanwhile, the reaction zone B, which neighbors the reaction zone A and is defined by the outer reaction tube 22, is packed with a catalyst different from the type of the catalyst layer stacked in the reaction zone A, thus forming a second catalyst layer 32'. Under the second catalyst layer 32', a catalyst layer different from that of the reaction zone A may be formed, and particularly, catalyst layers in which, when the reaction zone A is formed with the FTS catalyst, the reaction zone B is packed with the RWGS catalyst, may be formed.

In addition, the catalytic reactor 20 includes a plurality of reaction zones defined by a plurality of partition walls, and a plurality of catalyst layers is formed by stacking the RWGS catalyst and the FTS catalyst in the plurality of reaction zones. As such, in order to maximize the contact area between the RWGS catalyst and the FTS catalyst, the catalyst layers stacked in one reaction zone defined as described above and in another, neighboring, reaction zone may be formed of different catalysts.

As an example therefor, as shown in FIG. 7, the catalytic reactor 20 includes four reaction zones C, D, E, F defined by three partition walls 26, 27, 28, and a plurality of catalyst layers 30" is formed by stacking the RWGS catalyst and the FTS catalyst in the four reaction zones. Specifically, when the reaction zone C of the catalytic reactor defined by the first partition wall 26 is packed with the RWGS catalyst to form a first catalyst layer 31", a second catalyst layer 32" may be formed by packing the FTS catalyst in the reaction zone D of the catalytic reactor that neighbors the reaction zone C and is defined by the second partition wall 27, and a third catalyst layer 33" may be formed by packing the RWGS catalyst in the reaction zone E of the catalytic reactor that neighbors the reaction zone D and is defined by the third partition wall 28. A fourth catalyst layer 34" may be formed by packing the FTS catalyst in the remaining reaction zone F, which neighbors the reaction zone E.

Here, the types of the catalyst layers that are stacked, the number of repetitions, and the formation of the reaction zones may vary depending on the production capacity, supply amount, and catalyst, and may be adjusted through various methods known to those skilled in the art.

Moreover, the catalyst layers are configured such that RWGS catalyst layers and FTS catalyst layers are formed adjacent to each other, whereby the reaction heat generated in the Fischer-Tropsch synthesis reaction may be efficiently supplied to the RWGS catalyst layers, thus increasing energy efficiency.

The RWGS catalyst and the FTS catalyst are preferably used in a form in which an active metal is supported on a support. Here, the active metals that are used may be the same as each other, but different active metals are preferably used.

The temperature of the carbon monoxide generator may be maintained at 300° C. to 475° C. through heat exchange between the RWGS catalyst and the FTS catalyst, and the catalyst pressure is preferably 5 bar to 50 bar. If the temperature and the pressure are less than the respective lower limits, the reactive gas may be insufficiently converted. On the other hand, if the temperature and the pressure exceed the respective upper limits, energy efficiency may be deteriorated due to excessive operation of a compressor for carbon deposition and pressure increase.

The remover 110 for separating and removing, from carbon monoxide, at least one of water and a hydrocarbon generated through the reverse water gas shift reaction and the Fischer-Tropsch synthesis reaction in the carbon monoxide generator may be disposed downstream of the carbon monoxide generator 100 of the present disclosure. The device embodying the remover 110 may perform separation through various techniques known in the art. For example, it may include, but is not limited to, a condenser that cools and separates the reaction product.

Here, the carbon monoxide and hydrocarbon separated from water, etc. may be supplied to the hydrocarbon generator 120 disposed downstream of the remover, thus yielding a high-grade hydrocarbon.

The hydrocarbon generator 120 may be packed with an FTS catalyst to perform a Fischer-Tropsch synthesis reaction. As such, the FTS catalyst may be the same as or different from the FTS catalyst of the carbon monoxide generator.

Moreover, the hydrocarbon generator 120 may operate under conditions of a temperature of 200° C. to 350° C. and a reaction pressure of 10 to 50 bar. If the temperature and the pressure of the hydrocarbon generator are less than the respective lower limits, the reaction rate may decrease due to the low temperature thereof, and the formation of a long-chain hydrocarbon is limited due to thermodynamic equilibrium under low pressure. On the other hand, if the temperature is higher than the upper limit, the length of the carbon chain may be shortened and thus the liquid hydrocarbon yield may decrease, and if the pressure exceeds the upper limit, there may arise a design problem in which the thickness of the outer wall of the reactor has to be increased in order to withstand the pressure.

Another aspect of the present disclosure pertains to a method of converting carbon dioxide to produce a hydrocarbon through hydrogenation of carbon dioxide using the system for converting carbon dioxide as described above.

The method of converting carbon dioxide according to the present disclosure may include generating carbon monoxide by introducing carbon dioxide and hydrogen into a reactor packed with both a RWGS catalyst and an FTS catalyst in order to increase the CO yield at a relatively low temperature.

In an embodiment of the present disclosure, the method of the present disclosure may further include removing at least one of a hydrocarbon and a byproduct such as water or the like from a reaction product generated in the step of generating carbon monoxide and producing a hydrocarbon by subjecting the reaction product from which the byproduct or the like is removed as described above to a Fischer-Tropsch synthesis reaction.

In the method of converting carbon dioxide, the carbon dioxide gas and hydrogen gas introduced into the system for converting carbon dioxide may be mixed at various ratios. In a specific embodiment of the present disclosure, hydrogen gas and carbon dioxide gas may be mixed at a molar ratio of 2:1 to 10:1.

Moreover, the carbon dioxide gas and hydrogen gas may be supplied to the catalytic reactor at various flow rates, and the flow rate and the gas hourly space velocity (GHSV) may be varied as known in the art. In a specific embodiment of the present disclosure, the GHSV may be 500 $h^{-1}$ to 20,000 $h^{-1}$, and preferably about 1,000 $h^{-1}$ to 5,000 $h^{-1}$.

According to the present disclosure, in the step of generating carbon monoxide, the reactor of the carbon monoxide generator is packed with both the RWGS catalyst and the FTS catalyst, whereby the carbon monoxide yield may be increased at a low temperature compared to when the RWGS catalyst is used alone.

Also, when the reaction heat of the FTS reaction is directly used for the RWGS reaction, a portion that is locally heated is not formed in the reactor, and the temperature gradient between the top/bottom and the inside/outside of the reactor is small, thus preventing thermal cracking. The supply of heat energy to the carbon monoxide generator may be minimized or eliminated, thereby maximizing the energy efficiency of the entire process.

The system and method for converting carbon dioxide according to the present disclosure may be described in more through the following examples, but the present detail disclosure is not limited thereto.

Example 1

The effect on the mixing ratio of the RWGS catalyst and the FTS catalyst was first observed. In a total mass of 0.4 g of a catalyst layer, 0.3 g of a mixed catalyst (represented by 100Fe-13Cu-12Al-15K), prepared so as to contain 100 parts by weight of Fe, 13 parts by weight of Cu, 12 parts by weight of Al, and 15 parts by weight of K based on the mass of the element, serving as an FTS catalyst, and 0.1 g of a RWGS catalyst (represented by 1 Pt—$Ce_2O$), prepared by supporting 1 wt % of Pt on a $Ce_2O$ support, were uniformly mixed together. These two catalysts were uniformly mixed with 2 g of a diluent (alpha alumina) and were then charged in a ½-inch stainless-steel fixed-bed reactor (carbon monoxide generator) as shown in FIG. 2. Before starting the reaction, the catalyst charged in the reactor was reduced with hydrogen at a flow rate of 2000 mlh$^{-1}$ gcat$^{-1}$ at 400° C. for 2 hr. Hydrogen and carbon dioxide were supplied at a flow rate of 4500 mlh$^{-1}$ gcat$^{-1}$ at a molar ratio of 3:1 into the reactor in which the catalyst layer was formed, and the reaction was carried out under conditions of a reaction temperature of 300° C. to 450° C. and a reaction pressure of 25 bar. The composition of the resulting product was analyzed through On-line GC (TCD, FID) depending on the reaction temperature, and the results thereof are shown in Table 1 below.

Example 2

In a total mass of 0.4 g of a catalyst layer, 0.2 g of an FTS catalyst having a composition ratio of 100Fe-13Cu-12Al-15K and 0.2 g of a RWGS catalyst having a composition ratio of 1 Pt—$Ce_2O$ were mixed. The remaining conditions were the same as in Example 1, and the carbon dioxide conversion reaction was carried out, and the results thereof are shown in Table 1 below.

Example 3

In a total mass of 0.4 g of a catalyst layer, 0.1 g of an FTS catalyst having a composition ratio of 100Fe-13Cu-12Al-15K and 0.3 g of a RWGS catalyst having a composition ratio of 1 Pt—$Ce_2O$ were mixed. The remaining conditions were the same as in Example 1, and the carbon dioxide conversion reaction was carried out, and the results thereof are shown in Table 1 below.

Comparative Example 1

A catalyst layer was formed by charging a mixture of 0.4 g of a RWGS catalyst having a composition ratio of 1 Pt-$Ce_2O$ and 2 g of a diluent (alpha alumina) in a ½-inch stainless-steel fixed-bed reactor, as shown in FIG. 2. Before starting the reaction, the catalyst charged in the reactor was reduced with hydrogen at a flow rate of 2000 mlh$^{-1}$ gcat$^{-1}$ at 400° C. for 2 hr. Carbon dioxide and hydrogen were supplied at a flow rate of 4500 mlh$^{-1}$ gcat$^{-1}$ at a molar ratio of 3:1 into the reactor in which the catalyst layer was formed, and the carbon dioxide conversion reaction was carried out under conditions of a reaction temperature ranging from 200° C. to 500° C. and a reaction pressure of 25 bar. The composition of the resulting product was analyzed through On-line GC (TCD, FID) depending on the reaction temperature, and the results thereof are shown in Table 1 below.

The $CO_2$ conversion represents the molar ratio of the converted $CO_2$ relative to the fed $CO_2$, and the CO yield represents the molar ratio of the $CO_2$ converted into CO among the fed $CO_2$.

TABLE 1

| Reaction temperature (° C.) | Example 1 (RWGS:FTS = 0.25:0.75) | | Example 2 (RWGS:FTS = 0.5:0.5) | | Example 3 (RWGS:FTS = 0.75:0.25) | | Comparative Example 1 (RWGS 100%) | |
|---|---|---|---|---|---|---|---|---|
| | $CO_2$ conversion | CO yield | $CO_2$ conversion | CO yield | $CO_2$ conversion | CO yield | $CO_2$ conversion | CO yield |
| 300 | 20.53 | 9.92 | 18.82 | 13.79 | 15.36 | 13.95 | 5.11 | 4.99 |
| 350 | 29.05 | 13.25 | 25.29 | 22.85 | 24.36 | 22.62 | 14.09 | 14.09 |
| 400 | 32.22 | 25.70 | 31.98 | 31.18 | 32.37 | 31.39 | 25.61 | 24.40 |
| 450 | 39.46 | 36.00 | 39.69 | 36.50 | 39.37 | 35.46 | 36.62 | 33.38 |

As is apparent from Table 1, the RWGS catalyst and the FTS catalyst were mixed together, whereby $CO_2$ conversion was increased and the CO yield was also increased compared to Comparative Example 1. This effect is remarkable when the amount of the RWGS catalyst falls in the range of 50% or more to less than 100% based on the total mass of the catalyst layer, as in Example 2 and Example 3, and when the reaction temperature is in the range of 300-400° C. In particular, at 400° C. in Example 2, the $CO_2$ conversion reached 32%, of which the rate of conversion into CO, that is, the selectivity for CO, reached about 98%, indicating that $CO_2$ conversion is high and the generation of byproducts other than CO is very low.

Example 4

The effect of the method of forming the catalyst layer on the reaction was observed. A first catalyst layer was formed by charging a mixture of 0.2 g of a RWGS catalyst having a composition ratio of 1 Pt—$Ce_2O$ and 1 g of a diluent (alpha alumina) in a ½-inch stainless-steel fixed-bed reactor as shown in FIG. 3, and a second catalyst layer was formed by charging a mixture of 0.2 g of an FTS catalyst having a composition ratio of 100Fe-13Cu-12Al-15K and 1 g of a diluent (alpha alumina) under the first catalyst layer. The conditions used in the reaction test were the same as in Example 1. The results thereof are shown in Table 2 below.

Example 5

A first catalyst layer was formed by charging a mixture of 0.2 g of an FTS catalyst having a composition ratio of 100Fe-13Cu-12Al-15K and 1 g of a diluent (alpha alumina) in a ½-inch stainless-steel fixed-bed reactor as shown in FIG. 3, and a second catalyst layer was formed by charging a mixture of 0.2 g of a RWGS catalyst having a composition ratio of 1 Pt—$Ce_2O$ and 1 g of a diluent (alpha alumina) under the first catalyst layer. The conditions used in the reaction test were the same as in Example 1. The results thereof are shown in Table 2 below.

Example 6

A first catalyst layer was formed by charging a mixture of 0.1 g of a RWGS catalyst having a composition ratio of 1 Pt—$Ce_2O$ and 0.5 g of a diluent (alpha alumina) in a ½-inch stainless-steel fixed-bed reactor as shown in FIG. 3, and a second catalyst layer was formed by charging a mixture of 0.1 g of an FTS catalyst having a composition ratio of 100Fe-13Cu-12Al-15K and 0.5 g of a diluent (alpha alumina) under the first catalyst layer. Thereafter, a third catalyst layer was formed by charging a mixture of 0.1 g of the RWGS catalyst as in the first catalyst layer and 0.5 g of a diluent (alpha alumina) under the second catalyst layer, and a fourth catalyst layer was formed by charging a mixture of 0.1 g of the FTS catalyst as in the second catalyst layer and 0.5 g of a diluent (alpha alumina) under the third catalyst layer. The conditions used in the reaction test were the same as in Example 1. The results thereof are shown in Table 2 below.

Example 7

A first catalyst layer was formed by charging a mixture of 0.1 g of an FTS catalyst having a composition ratio of 100Fe-13Cu-12Al-15K and 0.5 g of a diluent (alpha alumina) in a ½-inch stainless-steel fixed-bed reactor, as shown in FIG. 3, and a second catalyst layer was formed by charging a mixture of 0.1 g of a RWGS catalyst having a composition ratio of 1 Pt—$Ce_2O$ and 0.5 g of a diluent (alpha alumina) under the first catalyst layer. Thereafter, a third catalyst layer was formed by charging a mixture of 0.1 g of the FTS catalyst as in the first catalyst layer and 0.5 g of a diluent (alpha alumina) under the second catalyst layer, and a fourth catalyst layer was formed by charging a mixture of 0.1 g of the RWGS catalyst as in the second catalyst layer and 0.5 g of a diluent (alpha alumina) under the third catalyst layer. The conditions used in the reaction test were the same as in Example 1. The results thereof are shown in Table 2 below. In Table 2 below, the $CO_2$ conversion and the CO yield were calculated as in Table 1.

TABLE 2

| Reaction temperature (° C.) | Example 4 | | Example 5 | | Example 6 | | Example 7 | | Comparative Example 1 | |
|---|---|---|---|---|---|---|---|---|---|---|
| | $CO_2$ conversion | CO yield | $CO_2$ conversion | CO yield | $CO_2$ conversion | CO yield | $CO_2$ conversion | CO yield | $CO_2$ conversion | CO yield |
| 300 | 21.98 | 12.38 | 10.61 | 10.61 | 10.89 | 10.89 | 12.62 | 12.02 | 5.11 | 4.99 |
| 350 | 29.51 | 15.67 | 27.17 | 15.82 | 23.16 | 18.44 | 25.55 | 17.72 | 14.09 | 14.09 |
| 400 | 33.82 | 31.40 | 38.34 | 15.39 | 31.14 | 29.91 | 33.88 | 26.58 | 25.61 | 24.40 |
| 450 | 40.28 | 38.37 | 44.85 | 13.80 | 39.93 | 37.44 | 40.23 | 32.28 | 36.62 | 33.38 |

As is apparent from Table 2, when the RWGS catalyst and the FTS catalyst were used together (Examples 4 to 7), it can be seen that $CO_2$ conversion was increased compared to Comparative Example 1, in which the RWGS catalyst was used alone.

Moreover, when the RWGS catalyst was used for the first layer (Examples 4 and 6), a high CO yield was exhibited at all reaction temperatures compared to Comparative Example 1. When the FTS catalyst was used for the first layer (Examples 5 and 7), the CO yield was similar to or lower than that of Comparative Example 1 at a reaction temperature of 400° C. or higher. This is deemed to be because the formation of a hydrocarbon by the FTS catalyst was activated early in the reaction, thus lowering CO selectivity.

Based on the above test results, the endothermic RWGS catalyst and the exothermic FTS catalyst were mixed in one reactor, and thus the heat generated by FTS was utilized as heat energy required for RWGS, thereby reducing the amount of energy consumed by the reactor or reducing the supply of energy from the outside. Also, it was confirmed that the $CO_2$ conversion and the yield and selectivity of the synthesized hydrocarbon were increased by changing the catalyst arrangement.

Since the carbon monoxide generator aims to increase the CO yield, the configuration in which the FTS catalyst and the RWGS catalyst are completely mixed without layer distinction (Examples 2 and 3) or the configuration in which the catalyst layer is divided into two or more such that the RWGS catalyst layer is disposed to first come into contact with the reactant and then the FTS catalyst layer and the RWGS catalyst layer are arranged alternately (Example 4 and Example 6) is advantageous.

The configurations of Example 5 and Example 7 can be advantageously applied when a low temperature is required for the reaction for conversion of $CO_2$, because $CO_2$ was completely converted into CO and almost no byproducts were generated at 300° C.

Although the present disclosure has been described with reference to the above-described embodiments and the accompanying drawings, different embodiments may be configured within the concept and scope of the present disclosure. Therefore, the scope of the present disclosure is determined by the appended claims and equivalents thereof, and is not limited by the specific embodiments described herein.

What is claimed is:

1. A system for converting carbon dioxide, suitable for converting carbon dioxide using hydrogen, comprising:
    a carbon monoxide generator comprising:
        a case having an inlet, into which carbon dioxide and hydrogen are introduced, formed in one side and an outlet, from which a reaction product is discharged, formed in an opposite side,
        a catalytic reactor disposed in an internal space of the case and packed with both a catalyst for a reverse water gas shift reaction and a catalyst for a Fischer-Tropsch synthesis reaction so that the reverse water gas shift reaction and the Fischer-Tropsch synthesis reaction are carried out together, thereby increasing a carbon monoxide yield and allowing reaction heat generated in the Fischer-Tropsch synthesis reaction to be used for the reverse water gas shift reaction,
    a remover disposed downstream of the carbon monoxide generator and receiving the reaction product from the carbon monoxide generator to separate and remove at least one of $H_2O$ and a hydrocarbon from the reaction product; and
    a hydrocarbon generator disposed downstream of the remover, packed with a catalyst for a further Fischer-Tropsch synthesis reaction, and receiving a gaseous material from the remover to carry out the further Fischer-Tropsch synthesis reaction to produce a high grade hydrocarbon.

2. The system of claim 1, wherein the catalyst for the Fischer-Tropsch synthesis reaction that is charged in the carbon monoxide generator is a catalyst comprising Fe and further comprising at least one selected from among Cu, K, Co, Zn and Al.

3. The system of claim 1, wherein the catalytic reactor of the carbon monoxide generator is configured such that a catalyst layer packed with the catalyst for the reverse water gas shift reaction and a catalyst layer packed with the catalyst for the Fischer-Tropsch synthesis reaction are repeatedly and alternately stacked one or more times, or such that the catalyst for the reverse water gas shift reaction and the catalyst for the Fischer-Tropsch synthesis reaction are uniformly mixed.

4. The system of claim 1, wherein the catalytic reactor of the carbon monoxide generator is configured such that an internal space thereof is divided into at least two reaction zones by a partition wall or a reaction tube, and each of the reaction zones is packed with the catalyst for the reverse water gas shift reaction or the catalyst for the Fischer-Tropsch synthesis reaction, reaction zones adjacent to each other being packed with different catalysts.

5. The system of claim 1, wherein the catalytic reactor of the carbon monoxide generator is configured such that an internal space thereof is divided into at least two reaction zones by a partition wall or a reaction tube, and a catalyst layer packed with the catalyst for the reverse water gas shift reaction and a catalyst layer packed with the catalyst for the Fischer-Tropsch synthesis reaction are repeatedly and alternately stacked one or more times in each of the reaction zones, catalyst layers located at a same height in reaction zones adjacent to each other being packed with different catalysts.

6. The system of claim 1, wherein, in the catalytic reactor of the carbon monoxide generator, the catalyst for the Fischer-Tropsch synthesis reaction and the catalyst for the reverse water gas shift reaction are present at a mass ratio ranging from 1:99 to 99:1.

7. The system of claim 1, wherein the catalyst for the reverse water gas shift reaction comprises at least one metal selected from the group consisting of Cu, Li, Rh, Mo, Pt, Ce and Pd.

8. A method of converting carbon dioxide, suitable for converting carbon dioxide using hydrogen, comprising:
    generating carbon monoxide by introducing carbon dioxide and hydrogen into a reactor packed with both a catalyst for a reverse water gas shift reaction and a catalyst for a Fischer-Tropsch synthesis reaction,
    separating and removing at least one of $H_2O$ and a hydrocarbon from a reaction product obtained in the generating the carbon monoxide; and
    producing a hydrocarbon using a catalyst for a further Fischer-Tropsch synthesis reaction from a gaseous material obtained after the removing the at least one of $H_2O$ and the hydrocarbon.

9. The method of claim 8, wherein the generating the carbon monoxide is performed at a reaction temperature of 300 to 475° C., and the producing the hydrocarbon is performed at a reaction temperature of 200 to 350° C.

10. The method of claim 8, wherein the generating the carbon monoxide is performed using a reactor configured such that the catalyst for the reverse water gas shift reaction and the catalyst for the Fischer-Tropsch synthesis reaction are uniformly mixed, or using a reactor configured such that a catalyst layer for the reverse water gas shift reaction and a catalyst layer for the Fischer-Tropsch synthesis reaction are repeatedly and alternately stacked one or more times, the catalyst layers being arranged such that carbon dioxide and hydrogen introduced into the reactor first come into contact with the catalyst layer for the reverse water gas shift reaction, wherein the catalyst for the reverse water gas shift reaction comprises at least one metal selected from the group consisting of Cu, Li, Rh, Mo, Pt, Ce and Pd, and the catalyst for the Fischer-Tropsch synthesis reaction that is charged in the carbon monoxide generator is a catalyst comprising Fe and further comprising at least one selected from among Cu, K, Co, Zn and Al.

* * * * *

UNITED STATES PATENT AND TRADEMARK OFFICE
CERTIFICATE OF CORRECTION

| | | |
|---|---|---|
| PATENT NO. | : 12,116,284 B2 | Page 1 of 1 |
| APPLICATION NO. | : 17/053577 | |
| DATED | : October 15, 2024 | |
| INVENTOR(S) | : Seok Ki Kim et al. | |

It is certified that error appears in the above-identified patent and that said Letters Patent is hereby corrected as shown below:

In the Claims
Claim 1, Column 16, Lines 8 and 9, "Fischer-Tropsch synthesis reaction to produce a high grade hydrocarbon." should be changed to -- Fischer-Tropsch synthesis reaction. --

Signed and Sealed this
Twenty-fourth Day of December, 2024

Derrick Brent
*Acting Director of the United States Patent and Trademark Office*